United States Patent [19]

Forquy et al.

[11] Patent Number: 5,166,362

[45] Date of Patent: Nov. 24, 1992

[54] PROCESS FOR THE MANUFACTURE OF THIOPHENE

[75] Inventors: Christian Forquy, Devon, Pa.; Michel Lacroix, Lyons; Michele Breysse, Caluire et Cuire, both of France

[73] Assignee: Societe Nationale Elf Aquitaine (Production), France

[21] Appl. No.: 748,405

[22] Filed: Aug. 22, 1991

[30] Foreign Application Priority Data

Aug. 29, 1990 [FR] France .................. 90 10762

[51] Int. Cl.$^5$ .................................. C07D 333/10
[52] U.S. Cl. ...................................... 549/83
[58] Field of Search ............................ 549/83, 85

[56] References Cited

U.S. PATENT DOCUMENTS

| | | | |
|---|---|---|---|
| 2,440,671 | 5/1949 | Boyd, Jr. .................. | 549/83 |
| 2,694,075 | 11/1954 | Ruidisch et al. .......... | 549/83 |
| 3,822,289 | 7/1974 | Clark et al. .............. | 549/85 |
| 3,939,179 | 2/1976 | Bell et al. ................ | 549/85 |
| 4,143,052 | 3/1976 | Barrault et al. .......... | 549/85 |

FOREIGN PATENT DOCUMENTS

| | | | |
|---|---|---|---|
| 502984 | 8/1948 | Canada .................... | 549/83 |
| 887426 | 1/1962 | United Kingdom ........ | 549/83 |

OTHER PUBLICATIONS

M. La Croix, et al., *Journal of Catalysis*, 120 (2) pp. 473-477 (1989).

T. S. Sukharova et al., "An Investigation of the Mechanism or Formation of Thiophene in the Presence of Sulphide Catalysts", Geterogennyi Kataliz, 2. Varna, 1979.

*Primary Examiner*—Richard L. Raymond
*Assistant Examiner*—Mark W. Russell
*Attorney, Agent, or Firm*—Morgan & Finnegan

[57] ABSTRACT

The invention relates to the manufacture of thiophene by catalytic dehydrogenation of tetrahydrothiophene.

Ruthenium sulphide, optionally mixed with sulphides of one or more other transition metals is employed as bulk or supported catalyst.

16 Claims, No Drawings

PROCESS FOR THE MANUFACTURE OF THIOPHENE

FIELD OF THE INVENTION

The present invention relates to the manufacture of thiophene by catalytic dehydrogenation of tetrahydrothiophene.

Applications of thiophene as an intermediate for the synthesis of pharmaceutical products (antihistamines, platelet anticoagulants, cephalosporins, antiinflammatories, and the like), of stabilizers for polymers and of colorants (diazothiophene) are numerous and rapidly growing.

BACKGROUND OF THE INVENTION

There are many methods of manufacture of thiophene, the starting materials being very varied:

- 1-butene or butadiene and $CS_2$ (French Patent No. 2,139,177),
- butane or 1-butene, $H_2S$ and sulphur (French Patent No. 2,242,391),
- butanediol and vaporized sulphur (Belgium Patent No. 671,591),
- n-butanol or 1,4-butanediol and CS: (French Patent No. 2,139,177),
- crotonaldehyde and $H_2S$ (French Patent No. 2,375,227),
- furan and $H_2S$ (Belgium Patent No. 623,801).

This last process is industrial but it requires a cheap supply of furan, which is not the case in most of the world. The other processes present problems of selectivity as a result of the formation of many undesirable products. In addition, they are catalytic processes in which rapid coking of the catalysts is observed, and this requires frequent regeneration.

A starting material which is particularly attractive for the manufacture of thiophene is tetrahydrothiophene (referred to by the initials THT hereinafter), whose industrial synthesis is carried out by starting with tetrahydrofuran, a low-cost raw material. A plant for the manufacture of thiophene can be advantageously placed following an industrial synthesis of THT from tetrahydrofuran, without requiring an excessively great capital cost. In addition, THT can be easily separated from thiophene; it is therefore unnecessary to work at total conversion and this allows the output of the industrial unit to be adapted to the demand.

The dehydrogenation of THT has formed the subject of several investigations. It is known, in fact, to employ oxides of aluminum and of cobalt or of aluminum, cobalt and molybdenum as a catalyst for this reaction (R. D. Obolentsev, Khim. Seroorgan. Soedin. Soderzhasch. v. Nelft. 1 Nefteprod. Akad. Nauk USSR, Bashkirsk. Filial 4, 245-255, 1961 and Bashkirsk. Filial 7, 148-155, 1964), but good yields are obtained in the first moments of the reaction and are not permanent. The activity of the catalyst drops very quickly because of coking, which blocks the dehydrogenation reaction.

Oxidative dehydrogenation of THT with $SO_2$ in the presence of a catalyst (metal oxide, activated alumina or active carbon) is derived in French Patent No. 2,071,189. It is indicated therein that the best results are obtained above all between 500 and 600° C. and that, when the temperature is too low, deactivation of the catalyst is considerable, chiefly as a result of the sulphur condensation, and that, moreover, decoking is incomplete.

In a paper titled "Study of the mechanism of thiophene formation in the presence of sulfide catalysts" (Geterog. Katal. 1979, 4th, pt. 2, 237-42; Chemical Abstracts, vol. 93, 131779d), T. S. SUKHAREVA, et al. teach that the most active catalysts are the sulphides of rhenium, molybdenum, iron, and platinum."

DESCRIPTION OF THE INVENTION

It has now been found that ruthenium sulphide is much more active and highly selective for the dehydrogenation of THT. Use of ruthenium sulphide-based catalysts enables the dehydrogenation to be carried out at relatively low temperatures and the activity of the catalyst to be stabilized over a longer period.

The subject of the invention is therefore a process for the manufacture of thiophene by catalytic dehydrogenation of THT, characterized in that a gaseous stream of THT is passed over a catalyst based on ruthenium sulphide.

This sulphide is very active in bulk form. However, for reasons of convenience of use on an industrial scale, it is preferred to employ it in the form of supported catalysts whose ruthenium content may range from 2 to 60% by weight, preferably from 2 to 20% and more particularly from 5 to 15%. The support may be, for example, an alumina, a silica, kieselguhr, titanium, or zirconium oxide, a silica-alumina, thorium oxide or an active carbon.

It would not constitute a departure from the scope of the present invention by using a mixture of sulphides of ruthenium and of at least one other transition metal selected from the group consisting of the following metals: vanadium, chromium, molybdenum, rhodium, palladium, tungsten, manganese, niobium, nickel, iron or cobalt, it being possible for the proportion of metal other than Ru in the mixture to be up to 80 by weight.

The preparation of the sulphides, whether supported or otherwise, can be carried out according to various methods which are known per se, such as, for example, the following:

Bulk catalysts:
  precipitation by addition of sodium sulphide to a methanolic solution of metal chloride(s), then extraction of the sodium chloride and finally treatment of the solid at a temperature of between 300° and 600° C., preferably at approximately 400° C. in the presence of a mixture of hydrogen and $H_2S$ (2 to 50% by volume, preferably approximately 15%).

Supported catalysts:
  impregnation of the support with one or more metal salts, for example chloride(s), followed by direct sulphurization with a mixture of hydrogen and $H_2S$ (2 to 50% by volume, preferably approximately 15%) or with $H_2S$ diluted in an inert gas (for example nitrogen) at a temperature of between 300° and 700° C., preferably between 400° and 600° C. and more particularly at approximately 500° C.

The temperature treatments with $H_2S$+diluent (hydrogen or inert gas) mixtures are preferably carried out in the reactor for producing thiophene, after the catalyst has been placed therein in a suitable form, for example in the form of tablets obtained by techniques which are known per se.

The conditions in which the reaction of dehydrogenation of THT is carried out can vary within wide limits without detriment to obtaining a high yield of thiophene, provided that this is done at a temperature and at partial pressures of THT and $H_2S$ which do not limit the shift of the thermodynamic equilibrium towards the total formation of thiophene. The operation may be carried out at a temperature of between 300° and 600° C., but is preferably carried out between 350° and 450° C. and more particularly between approximately 380° and 420° C. The reaction may be carried out at atmospheric pressure or at a higher pressure which can be up to 15 bars absolute. The contact time may vary between 0.1 and 10 seconds and is preferably between 1 and 3 seconds.

Inert diluents such as, for example, rare gases or nitrogen be employed to limit the partial pressure of THT in the gas stream passing over the catalyst. However, it is preferred to dilute THT with $H_2S$ in an $H_2S$/THT molar ratio ranging from 0.1 to 10, preferably 1 to 5 and especially of approximately 4.

EXAMPLES

The following examples illustrate the invention without limiting it.

EXAMPLE 1

A series of unsupported sulphides of transition metals were prepared by employing the operating procedures described in the literature (J. Catal., Vol. 120, p. 473, 1989).

The sulphides thus synthesized were tested in the reaction of dehydrogenation of tetrahydrothiophene under the following conditions:
Temperature 380° C.
Total pressure 1 bar
Partial pressure of THT 6.6 $10^2$ Pa
Partial pressure of $H_2S$ 6.6 $10^2$ Pa A tubular glass microreactor 30 ml in volume was employed, containing a mass of catalysts of between 50 and 300 mg and operating continuously, the overall flow rate being generally 60 ml. The THT was introduced into the reaction enclosure by means of a saturator-condenser kept at constant temperature, the latter determining the partial pressure of THT. Analysis of the gaseous effluents leaving the reactor was carried out using gas phase chromatography.

The catalyst activities determined in a pseudostationary state are summarized in the following table.

The activity of ruthenium sulphide according to this invention is far better than that of the other metal sulphides tested.

TABLE 1

Catalytic properties of unsupported transition metal sulphides in the reaction of dehydrogenation of tetrahydrothiophene.

| Metal sulphide | Specific activity $10^{-8}$ mol s$^{-1}$ g$^{-1}$ | Specific surface m$^2$/g | Intrinsic activity $10^{-8}$ mol s$^{-1}$ m$^{-2}$ | Selectivity for thiophene, % |
|---|---|---|---|---|
| V | 27.6 | 46 | 0.6 | 93 |
| Cr | 172 | 160 | 1.1 | 94 |
| Mn | 1.4 | 6 | 0.2 | 62 |
| Fe | 3 | 5 | 0.6 | 60 |
| Co | 8 | 28 | 0.3 | 80 |
| Nb | 4 | 15 | 0.3 | 86 |
| Mo | 12 | 8 | 1.5 | 96 |
| Ru | 490 | 40 | 12.3 | 97 |
| Rh | 56 | 9.3 | 6 | 96 |
| Pd | 24 | 14 | 1.7 | 90 |
| W | 25 | 17.6 | 1.4 | 92 |
| Zn | 5.2 | 11 | 0.5 | 24 |
| Ni | ε | — | ε | — |

TABLE 1-continued

Catalytic properties of unsupported transition metal sulphides in the reaction of dehydrogenation of tetrahydrothiophene.

| Metal sulphide | Specific activity $10^{-8}$ mol s$^{-1}$ g$^{-1}$ | Specific surface m$^2$/g | Intrinsic activity $10^{-8}$ mol s$^{-1}$ m$^{-2}$ | Selectivity for thiophene, % |
|---|---|---|---|---|
| Cd | ε | — | ε | — |

EXAMPLE 2

Three alumina-supported catalysts were prepared by impregnating a transition alumina with various salt precursors of vanadium, molybdenum or ruthenium sulphide. In the case of the catalysts based on vanadium and molybdenum, ammonium thiovanadate and ammonium heptamolybdate were employed respectively. In the case of the ruthenium-based catalyst, ruthenium chloride was employed, which makes it possible to obtain a better dispersion and a higher sulphurizability of ruthenium.

The alumina employed is a cubic gamma-alumina, preformed in the form of 1.2-mm extrudates. Its specific surface area is 232 m$^2$/g and this support has a pore volume of 0.64 cm$^3$/g. The loss on ignition at 1000° C. is 2.1%.

This support, predried at a temperature of between 100 and 250° C., preferably at 180° C., is brought into contact with an aqueous solution of the metal salt corresponding to the desired catalyst. The quantity of water employed is equal to the pore volume of the support, but an excess of water which may be up to three times that needed to fill the pores of the support may be optionally employed without disadvantage.

After drying between 100° and 200° C., the precursors were sulphurized by treatment at 400° C. for 4 hours by means of a mixture of $H_2S$ and nitrogen (in the case of Ru) or of hydrogen (in the case of Mo and V), the $H_2S$ content being of the order of 15% by volume.

The supported catalysts thus obtained were then tested in the reaction of dehydrogenation of THT under the same conditions as in Example 1. The results obtained are collated in Table 2 below in which the second column shows the weight content of metal (Mo, V or Ru) of the supported catalyst.

TABLE 2

Properties of the alumina-supported sulphides.

| Catalyst | % metal | Specific activity $10^{-7}$ mol s$^{-1}$ g$^{-1}$ | Selectivity for thiophene, % |
|---|---|---|---|
| Mo/Al$_2$O$_3$ | 10.6 | 1.2 | 70 |
| V/Al$_2$O$_3$ | 9 | 2.4 | 80 |
| Ru/Al$_2$O$_3$ | 7 | 18 | 92 |

These results show that the remarkably good dehydrogenation properties obtained with unsupported ruthenium sulphide are maintained when ruthenium sulphide is dispersed on a support such as alumina.

EXAMPLE 3

The influence of the conditions of activation of the Ru/Al$_2$O$_3$ catalyst (7% Ru by weight) was studied by running the catalyst test under the same operating conditions as those employed in the preceding example. The activities and selectivities obtained for different temperatures of activation of the catalyst with an N$_2$H$_2$S mixture (15 vol% $H_2S$) are listed in Table 3 below:

TABLE 3

Activities and selectivities as a function of activation temperature.

| Activation temperature | Specific activity $10^{-7}$ mol/s/g | Selectivity for thiophene, % |
|---|---|---|
| 400° C. | 18 | 92 |
| 500° C. | 40 | 90 |
| 600° C. | 30 | 85 |

EXAMPLE 4

The results listed in Examples 1 and 2 show the superiority of the $RuS_2$ pyrites phase, whether supported or otherwise. The $RuS_2/Al_2O_3$ catalyst containing 7% of Ru by weight was therefore tested on micropilot scale under the following operating conditions:

| | |
|---|---|
| THT flow: | 0.33 mol/h |
| $H_2S$ flow: | variable |
| Catalyst mass: | 38 g |
| Reaction temperature: | 380° C. |
| Total pressure: | 1 bar |

The function of the $H_2S$ addition is, on the one hand, to limit the secondary reactions leading to the formation of hydrocarbons by rupture of the C-S bond and, on the other hand, to dilute the reactant in order to increase the limiting conversion imposed by thermodynamics. In addition, the presence of hydrogen sulphide enables the catalyst to be maintained in the form of sulphide.

The reactor employed is a stationary bed reactor consisting of a vertical tube of 316 stainless steel 800 mm in length and 25 mm in diameter, fitted with a thermometric sheath permitting an accurate control of the temperature profile along the catalyst bed. THT is introduced in the liquid state by means of a pump and encounters $H_2S$ in a preheater situated upstream of the reactor and maintained at 150° C. to permit a fast volatilization of THT. On leaving the reactor, the liquid phase is recovered in condensers.

The influence of the $H_2S$/THT molar ratio on the selectivity for thiophene was studied under operating conditions resulting in an overall conversion of the order of 30%. Table 4 summarizes the results obtained.

TABLE 4

Effect of the $H_2S$/THT ratio on the distribution of the reaction products.

| $H_2S$/THT molar ratio | Overall Conversion % | Selectivity C1 + C2 + C3 % | C4 % | Thiophene % |
|---|---|---|---|---|
| 1 | 35 | 10 | 30 | 60 |
| 1.6 | 32 | 7 | 26 | 67 |
| 2 | 31 | 5 | 21 | 74 |
| 4 | 32 | 4 | 18 | 78 |

EXAMPLE 5

The behavior of the $RuS_2/Al_1O_3$ catalyst with time was studied under the same operating conditions as in the preceding example, a $H_2S$/THT ratio of 2 being employed. The change in the conversion and selectivity for thiophene as a function of catalyst working time is given in the following table:

TABLE 5

Study of the aging of the $RuS_2/Al_2O_3$ catalyst.

| Time (h) | Overall conversion (%) | Selectivity for thiophene (%) |
|---|---|---|
| 25 | 90 | 74 |
| 35 | 86 | 74 |
| 80 | 77 | 75 |
| 100 | 74 | 74 |
| 120 | 71 | 73 |
| 140 | 61 | 74 |
| 165 | 55 | 73 |
| 200 | 49 | 74 |
| 250 | 34 | 73 |
| 320 | 16 | 74 |

These results show that the catalyst is deactivated linearly in the course of working time without any change in selectivity being observed. Under the operating conditions employed the half-life of the solid is of the order of 200 hours.

EXAMPLE 6

The catalyst originating from the preceding example contains a proportion of "coke" of the order of 17% by weight. To remove the latter the spent catalyst is subjected to a treatment of regeneration with air or with a mixture of air and water (air/water molar ratio=20). This oxidizing treatment is performed at 350° C. with a catalyst-air (or air+water) contact time of approximately 3 seconds.

At the end of this treatment the sulphide phases, converted into oxides or into oxosulphides, are resulphurized by treatment with an $H_2S/N_2$ mixture under the same conditions as in Example 2.

The results obtained with the regenerated catalysts are listed in the following table:

TABLE 6

Catalyst properties of regenerated catalysts.

| Regenerating atmosphere | Initial conversion (25 hours) | Conversion after 150 hours | Selectivity for thiophene, % |
|---|---|---|---|
| air | 85% | 55% | 74 |
| air + water | 88% | 60% | 74 |

As a general rule, the regenerating treatment can be carried out at a temperature of between 300° and 600° C., preferably between 350° and 400° C., with a contact time of between 0.1 and 10 seconds. When a mixture of air+water is employed, the air/water molar ratio may range from 1 to 40.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the manufacture of thiophene by catalytic dehydrogenation of tetrahydrothiophene, comprising passing a stream of gaseous tetrahydrothiophene over a catalyst based on ruthenium sulphide.

2. Process according to claim 1, wherein ruthenium sulphide is employed in bulk form.

3. Process according to claim 1, wherein ruthenium sulphide is deposited on a support.

4. Process according to claim 3, wherein the support is an alumina, a silica, kieselguhr, titanium or zirconium oxide, a silica-alumina, thorium oxide or an active carbon.

5. Process according to claim 3, wherein the ruthenium content of the supported catalyst is between 2 and 60% by weight.

6. Process according to claim 1, wherein the dehydrogenation is performed at a temperature of between 300° and 600° C.

7. Process according to claim 1, wherein the reaction is performed at a pressure between atmospheric pressure and up to 15 bars absolute.

8. Process according to claim 1, wherein the tetrahydrothiophene is diluted with an inert gas.

9. Process according to claim 1, wherein use is made of a mixture of sulphides of ruthenium and of at least one transition metal selected from the group consisting of the following metals: vanadium, chromium, molybdenum, rhodium, palladium, tungsten, manganese, niobium, nickel, iron, and cobalt, the proportion of metal other than ruthenium in the mixture to be up to 80 % by weight.

10. Process according to claim 5, wherein the content of supported catalyst is between 2 and 20%.

11. Process according to claim 5, wherein the content of supported catalyst is between 5 and 15%.

12. Process according to claim 6, wherein the temperature is between 350° and 450° C.

13. Process according to claim 6, wherein the temperature is between approximately 380° and 420° C.

14. Process according to claim 8, wherein dilution is with hydrogen sulphide in an $H_2S$/tetrahydrothiophene molar ratio from 0.1 to 10.

15. Process according to claim 14, wherein the molar ratio is between 1 and 5.

16. Process according to claim 15, wherein the molar ratio is approximately 4.

* * * * *